Figure 1:
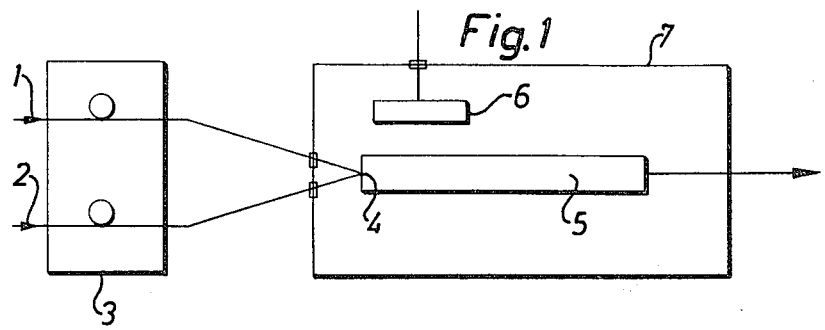

| United States Patent [19]
Wettermark et al.

[11] 3,962,029
[45] June 8, 1976

[54] METHOD OF CONTROLLING THE AMOUNT OF CHEMICALS IN LIQUIDS USED WITHIN THE CELLULOSE INDUSTRY AND RELATED INDUSTRIES

[75] Inventors: Karl Gustav Gunnar Wettermark, Taby; Per Ulf Isacsson, Vallentuna; Bengt Goran Hultman, Domsjoverken; Per Henrik Otto Johan Norberg, Sjalevad; Bo Nils Olof Lindahl, Domsjoverken, all of Sweden

[73] Assignee: Mo och Domsjo AB, Ornskoldsvik, Sweden

[22] Filed: Oct. 17, 1974

[21] Appl. No.: 515,735

[30] Foreign Application Priority Data
Oct. 17, 1973 Sweden................................ 7314129

[52] U.S. Cl.................................... 162/49; 162/50; 162/238; 162/252; 162/263; 162/DIG. 10; 252/186; 252/187 R; 252/188.3 CL; 252/301.16; 356/181
[51] Int. Cl.²........................................... D21C 7/14
[58] Field of Search............... 162/49, 50, 252, 263, 162/238, DIG. 10; 356/181, 250; 252/188.3 CL, 186, 187 R, 301.2 R

[56] References Cited
UNITED STATES PATENTS

| | | | |
|---|---|---|---|
| 3,366,572 | 1/1968 | Scott et al. | 252/188.3 CL |
| 3,539,794 | 11/1970 | Rauhut et al. | 252/188.3 CL |

*Primary Examiner*—S. Leon Bashore
*Assistant Examiner*—George C. Yeung

[57] ABSTRACT

A method is provided for controlling the amount of oxidizing bleaching agents in liquors used within the cellulose industry, as in the bleaching of sulphite, sulphate, mechanical, chemimechanical, semichemical or similar cellulose pulps, and in related industries, and particularly for controlling the addition of oxidizing bleaching agents to the system during the bleaching of cellulose pulp by mixing such liquor with at least one chemiluminescent reagent which reacts with the oxidizing bleaching agents in a manner to emit light. The amount of oxidizing bleaching agents in the liquor is then determined by comparison of the light intensity thus obtained with the light intensity for previously measured calibration values corresponding to known quantities of such oxidizing bleaching agents, and then from such determination controlling the addition of such oxidizing bleaching agents to the liquor.

15 Claims, 4 Drawing Figures

METHOD OF CONTROLLING THE AMOUNT OF CHEMICALS IN LIQUIDS USED WITHIN THE CELLULOSE INDUSTRY AND RELATED INDUSTRIES

The control of chemical processes in the cellulose industry at present largely utilizes pressure, temperature, flow rate, refractive index, conductivity, pH and redox potential measurements. Of these, only pH provides a specific measurement of a specific component, H+ ion concentration. Because of this, cellulose mills are encumbered with the high cost of having their operational laboratories do manual analyses on random samples of processing liquids and products. It is desirable to eliminate slow and expensive manually taken and manually analyzed random samples. What is required is a continuously operating, rapid and accurately working sensing means which is capable of selectively measuring the amounts of the desired substances.

A certain amount of development in this respect has taken place in recent years. For example, methods have been proposed for controlling a sulphate cooking process by automatic analysis of the hydroxide ion content of cooking liquor, and combining this information with known relationships between reaction time and cooking temperature. It is interesting to note that it was known for a long time how the hydroxide ion content, the reaction time and cooking temperature affected the final results, i.e. the quality of the unbleached pulp, but that it was not until a continuous hydroxide ion measuring method became available that a control method utilizing this development could be used in practice.

Otherwise, there are very few measuring methods in the cellulose industry in which the quantity of a specific component is measured, and this determination used for automatically and continuously controlling a process. Despite the fact that in a pulp mill large quantities of chemicals are handled, and large quantities of products are produced, control of the process is according to manual analytical determinations made on random samples, instead of an appropriate continuous measuring method. One reason is that the measuring instruments (analytical instruments) available are complicated, or expensive, or unreliable. A number of interesting devices, such as ion-selective electrodes, for example, are able to function satisfactorily in the laboratories, but in practice in a pulp mill give unstable and unreliable analysis, as a result of corrosion. Furthermore, the signal obtained from such an electrode, and also from a pH or redox electrode, is logarithmically dependent on the content of the substance to be measured, and a high degree of accuracy in the potential measurement is therefore required.

There is therefore a noticeable dearth of chemical measuring methods in use in the cellulose industry.

In the bleaching of cellulose pulp, the main objective is to increase the brightness of the pulp. Another objective, for example, when manufacturing highly bleached sulphite or sulphate pulp, is to remove as much as possible of the residual lignin present in the pulp after the pulping process.

The most important bleaching agents used in cellulose pulp bleaching processes are oxygen, chlorine dioxide, hypochlorite, and various types of peroxides, for example, hydrogen peroxide, sodium peroxide, or organic peroxy compound such as for example peracetic acid. It is also possible to use perborates, persulphates, or ozone. The distinguishing feature of these substances is that they are all strong oxidizing agents, and expensive, compared with pulping chemicals for sulphate or sulphite processes, for example. Because of their high price, pulp mills will not use more bleaching agent than is required to achieve the desired brightness of the finished pulp. Because of their strong oxidizing properties, an excess of such bleaching agents results in degradation of the cellulose, resulting in yield losses and an impaired quality of the pulp, i.e. a reduction in strength.

Because of variations in the conditions of a pulping process, and in the quality of the wood that is pulped, there is obtained in the manufacture of chemical pulp a varying content of lignin in the unbleached pulp. This means that the quantity of bleaching agent required for a certain quantity of pulp will vary. Consequently, it is impossible to control the quantity of bleaching agent charged to a flow of unbleached cellulose pulp solely by quotient control methods, i.e. by charging a constant amount of bleaching agent per volume of unbleached cellulose pulp to be treated. A better method is to measure the quantity of residual bleaching agent, at a suitable time after mixing bleaching agent and pulp. In this way it is possible to obtain a measurement of how much bleaching chemical has been consumed by the pulp, and to regulate the addition of bleaching agent with respect to this.

The methods hitherto used for this purpose include the measurement of the redox potential, and a number of polarographic methods. As previously mentioned, the disadvantage with redox measuring methods is that the signal from the electrode has a logarithmic relationship with the content of the substance which is to be measured.

The method is also unspecific. When measuring the chlorine content, for example, the signal obtained is also affected by the pH; the chloride ion content; the presence of other substances, such as chlorine dioxide; and the temperature. This means that a redox measuring process will only provide a good measurement of the component to be analyzed under very ideal conditions, for example under laboratory conditions. In practice, the redox measuring method must normally be considered as a comparative measuring method, which gives information as to whether a substance is present in relatively high or relatively low quantities.

The polarographic measuring methods are based on the measurement of the current created by electrolysis of the liquid to be analyzed. The intensity of the current is proportional to the concentration of current-transmitting ions. In the case of chlorine, for example, it is possible to measure the current which passes through the solution by way of the reaction which takes place at the anode:

$$Cl_2 + 2e^- \rightarrow 2\ Cl^-$$

However, the current intensity detected by this method depends not only on chloride ion $Cl^-$ but also on other ions present, which may be electrolysed simultaneously, and which also contribute to the current. The method is also dependent on temperature. During electrolysis, part of the substance to be analyzed is also consumed, and hence it is important that a fresh sample be constantly supplied to the electrolysis electrodes. For the diffusion of chlorine to the electrodes, a certain flow rate of the liquid which it is desired to analyze is required.

Chemical reactions in which light is emitted are used in this invention for the continuous analysis of bleaching liquors containing an oxidizing bleaching agent and other liquors used within the cellulose industry containing an oxidizing bleaching agent. The present invention in this way circumvents the disadvantages encountered with the aforementioned methods, and provides a method by which the amounts of oxidizing bleaching agents in liquors used in the cellulose industry and related industries, especially in chlorine, chlorate, and chlorine dioxide manufacture, particularly the amount of oxidizing bleaching agent in bleaching liquors, can be continuously and rapidly determined, thereby making possible control of a bleaching process and other processes utilizing oxidizing bleaching agents according to the amounts of such chemicals required.

That light is emitted in the course of chemical reactions has long been known. The phenomenon is referred to as chemiluminescence. The method used to determine the intensity of such emitted light involves the rapid mixture of a specific volume of the solution to be analyzed with a specific volume of reagent solution. This method has been applied batchwise, for example by rapidly injecting the sample into a vessel containing the reagent solution. The light thus emitted is registered as an electric signal, or through photographic techniques that measure the quantity of such light. This batchwise method is so slow, however, that, in a rapid industrial process, it does not allow one to follow the change in concentration of a specific component during the process. The method also requires apparatus which is both mechanically and electronically complicated, and expensive.

In accordance with the present invention, a method is provided for controlling the quantity of an oxidizing bleaching agent in a liquor used in the cellulose industry and related industries, which comprises continuously mixing such liquor with at least one chemiluminescent reagent which reacts with the oxidizing bleaching agent or agents in a manner to emit light; continuously measuring the intensity of such light, and, from such previously measured calibration values obtained from tests with known intensity determining the amount of such oxidizing bleaching agent in the liquor; and then from such determination controlling the addition of such oxidizing bleaching agent to the liquor.

In a preferred embodiment, a portion at least of the emitted light can be caused to impinge upon a photoelectric detector, which thereupon gives a signal whose response is related to the content of the chemical substance in the liquor.

The process of the invention is applicable to any liquor that contains an oxidizing bleaching agent for the treatment of cellulosic material, especially wood and like lignocellulosic material, and specifically bleaching liquor for the bleaching of cellulose pulp, in which the bleaching agent is also an oxidizing agent. Exemplary oxidizing bleaching agents are chlorine compounds, or mixtures thereof, such as chlorine, alkali metal hypochlorite and chlorine dioxide; and per compounds such as an alkali metal peroxide or perborate, or hydrogen peroxide, or a per acid, such as peracetic acid.

The method according to the invention is particularly suited for use with bleaching processes in the cellulose industry or in the manufacture of bleaching agents used in the cellulose industry.

The substances which can be determined in this way are, in particular, strongly oxidizing substances, for example, the chlorine compounds used in the bleaching of cellulose, i.e. chlorine, sodium hypochlorite, and chlorine dioxide. It is also possible to determine in the same way organic and inorganic peroxides, perborates, oxygen and ozone.

Examples of chemiluminescent reagents which are oxidized by and thereby emit light when admixed with oxidizing bleaching agents include "luminol", 1,3-aminophthalic acid hydrazide; "lucigenin", N, N'-dimethylacridinium dinitrate; and "lophin", 2,4,5-triphenyl imidazole.

The speed of reaction of the chemiluminescent reagent and the oxidizing bleaching agent to be analyzed can be increased by a catalyst for the reaction. A suitable catalyst is $CuCl_2$ cuprous chloride, but other Lewis acids and bases can also be used. Normally, however, a catalyst is not required, since the reaction between the chemiluminescent reagent and the oxidizing bleaching agent is rapid. The detection of the light emitted is also very rapid, and in terms of modern techniques can be considered to be practically instantaneous. The rapid reaction between reagent and the oxidizing bleaching agent and the rapid detection of the light emitted therewith makes it possible to make extremely rapid analyses. The only factor which limits the speed at which such analyses can be made is the time it takes to pump a sample of the bleaching liquor from the sampling point to the point where the bleaching liquor and the chemiluminescent reagent are mixed.

The present invention also provides the possibility of simultaneously analyzing for the amounts of several substances, which is an advantage since it is often required to use a mixture of two bleaching agents. Thus, during a bleaching process it may be an advantage to use simultaneously chlorine and chlorine dioxide. There is a difference in the reaction rate between chlorine and chlorine dioxide when reacting the same with, for example, luminol. When the bleaching liquor comes into contact with the chemiluminescent reagent solution, the chlorine dioxide will react at once, whereas the chlorine reacts more slowly. This means that the light emitted first, following mixing, gives a measurement of the chlorine dioxide content. Later on, when the chlorine dioxide is consumed, the light emitted gives a measurement of the chlorine content. Another method of simultaneously measuring in the same liquid the content of several substances of said liquid is to use a chemiluminescent reagent solution containing several chemiluminescent reagents, each reactive with a different substance, at a different rate of reaction.

The reaction of chlorine and chlorine dioxide and the chemiluminescent reagent is also pH dependent, and these oxidizing bleaching agents react therewith at different pH values. Consequently, one can also ensure separate reaction of chlorine and chlorine dioxide therewith by utilizing a pH at which only one of these agents reacts, and then utilizing a pH at which the other reacts.

FIG. 1 illustrates diagrammatically the construction of a measuring apparatus which can be used in the method according to the invention. With this apparatus the liquid to be analyzed is pumped through a line 1, while the chemiluminiscent reagent solution is passed through a line 2 by means of a pump 3. The liquid to be analyzed and the reagent are mixed at a point 4 of the system. The resulting mixture is caused to pass through a tube or bulb 5, and from there to an outlet. The light emitted by the liquid mixture at the mixture point and/or from the tube 5 is measured by a detector 6. The mixture point 4 and the tube 5 and detector 6 are enclosed in a light-tight box 7, so as to exclude external light.

When several substances are to be measured at the same time, several detectors can be placed at different distances from the mixing point. It is an advantage if the position of the several detectors can be adjusted relative to the mixing point and the tube 5.

Figure 2:
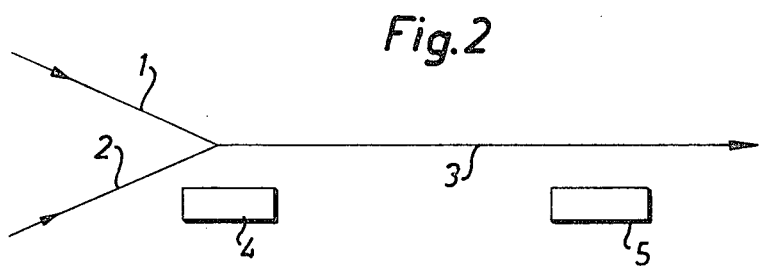
Figure 3:
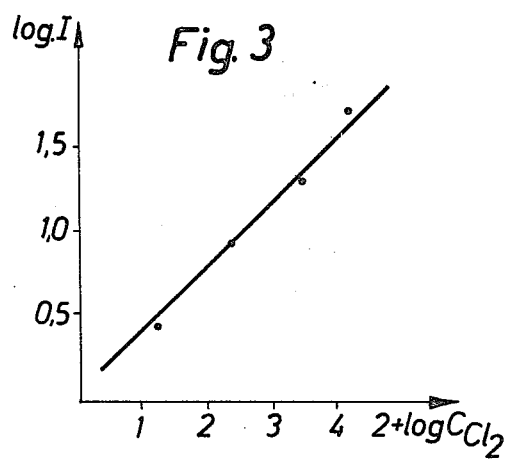
Figure 4:
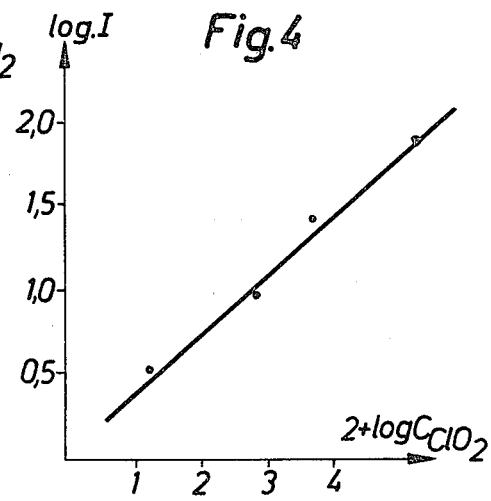

FIGS. 2–4 illustrate diagrammatically with reference to Example 1 hereinbelow, which show the application of chlorine and chlorine dioxide as the oxidizing substances in the system according to the invention.

The invention will now be illustrated more clearly with reference to the following Examples, which show the application of the invention to different processes in the cellulose industry.

EXAMPLE 1

The concentrations of chlorine and chlorine dioxide in an aqueous solution (liquid) were determined simultaneously by means of chemiluminescence. The reagent used was a mixture of luminol (concentration $6.5 \times 10^{-3}$ moles per liter), hydrogen peroxide (concentration $2 \times 10^{-3}$ moles per liter), and a carbonate buffer (pH = 10.3) containing 8.5 grams of sodium bicarbonate and 13.3 grams of sodium bicarbonate in 250 ml of water. The chemiluminescent reagent solution comprised 8 parts of luminol, one part of hydrogen peroxide, one part of carbonate buffer, and ten parts of water.

In accordance with the diagram shown in FIG. 2, the liquid 1 and the chemiluminescent reagent 2, each at a speed of 20 ml/min, were pumped together through a reaction capillary 3. A detector 4 for the chlorine dioxide was placed in the immediate vicinity of the point where the two flows met, while a detector 5 for the chlorine was placed 5 cm from the detector 4 downstream of the capillary 3.

A calibration was then made. The logarithm of the obtained reading on the detector in mV, corresponding to the logarithm for the light intensity, was plotted against the logarithm of the iodometrically-determined concentration in g/l (FIGS. 3 and 4).

In a series of mixtures of chlorine-chlorine dioxide with the chlorine dioxide content at a constant level of 0.020 g/l and chlorine concentrations at 0.010, 0.020, 0.025 and 0.030 g/l, the concentration was measured at room temperature by means of chemiluminescence. The following results were obtained:

| Chlorine (g/l) | Chlorine dioxide (g/l) |
| --- | --- |
| 0.010 | 0.022 |
| 0.021 | 0.020 |
| 0.024 | 0.018 |
| 0.032 | 0.021 |

In another series of mixtures of chlorine-chlorine dioxide, the chlorine content was held constant at 0.020 g/l and the chlorine dioxide contents were respectively 0.005, 0.010, 0.015 and 0.025 g/l. The following results were obtained:

| Chlorine (g/l) | Chlorine dioxide (g/l) |
| --- | --- |
| 0.018 | 0.006 |
| 0.021 | 0.009 |
| 0.020 | 0.015 |
| 0.019 | 0.024 |

As the results show, it is possible in accordance with the invention to determine the chlorine and chlorine dioxide contents continuously, rapidly and very accurately, either individually or combined in an aqueous solution.

The method according to the invention was used in the bleaching of sulphate pulp, to regulate the addition of both chlorine and chlorine dioxide in a bleaching stage where the two bleaching agents were used in admixture. These tests showed that the method of the present invention gave bleaching results as good as methods using conventional control procedures with manually taken samples and analyses.

As a result of the accurate control of the addition of bleaching agent, it was possible to reduce the consumption of both chlorine and chlorine dioxide by from 2 to 2.5 tons/day. In addition to the reduced consumption of chemicals, the services of a laboratory assistant could be saved.

EXAMPLE 2

In the bleaching section of a sulphite mill, where the bleaching sequence CEHD was used (C designates a chlorine stage, E an alkaline extraction stage, H a hypochlorite stage and D a chlorine dioxide stage); the chlorine stage was divided in two bleaching towers. In this stage the pulp concentration was 2.5 to 3.5%, and the chlorine charge 2 to 2.5% as active chlorine. In the line extending between the bleaching towers a special sampling device was arranged, from which a continuous flow of bleaching waste liquor was obtained. The main portion of fibers and resin particles was separated in the sampler. The waste bleaching liquor thus obtained was not, however, completely clear, but still contained a number of fiber fragments (zero fibers) and resin particles.

The chlorine content of the bleaching waste liquor was determined in a previously known manner by iodometric titration, and by means of the continuous chemiluminescence method. The reagents and the method by which this analysis was made were those described in Example 1. The following results were obtained:

| The chlorine content measured by iodometry ($Cl_2$, g/l) | The content of chlorine measured by chemiluminescence ($Cl_2$, g/l) |
| --- | --- |
| 0.043 | 0.046 |
| 0.049 | 0.046 |
| 0.032 | 0.032 |
| 0.014 | 0.010 |

The chlorine content could be determined with relatively good accuracy, despite the presence of resin and fiber particles and a number of chemicals from the cooking process and the bleaching process (in particular the presence of chlorinated lignin residues).

In order to test whether a regulation of the chlorine charge to the C-stage could be made, an apparatus according to FIG. 1 was coupled to a control circuit, the residual chlorine content in the pulp suspension being determined after a certain bleaching period had elapsed. This content was then used to control the addition of chlorine so that a constant residual chlorine content was obtained. By continuously controlling the chlorine charge to the chlorine stage (which is a very important bleaching stage, since the major part of the lignin which is removed during the bleaching stage is made soluble there), the conditions in the subsequent stages can be maintained more constant. This means that the number of adjustments which need be made become less, thereby saving cost, and also savings are made in the amounts of chlorine, hypochlorite and chlorine dioxide chemicals. It was also found that the quality of the pulp was more uniform. The chemical requirement was reduced by 1.5 tons chlorine per day.

EXAMPLE 3

In a mill for producing and bleaching mechanical pulp, hydrogen peroxide was used as a bleaching agent. To contain pollutants, and meet requirements on the care and protection of the environment, the mill was equipped with a closed recirculating liquid system. The waste bleaching liquor obtained in the peroxide bleaching process was returned to the grinding process, and was cycled between the grinding process and the bleaching process a number of times before it was discharged.

A suitable point to measure the content of peroxide was in the liquid separated from the pulp on the wet lap forming machine where sheeted pulp was manufactured. In the laboratory, the hydrogen peroxide content of the pure aqueous solution was determined by titration with permanganate and by means of continuous chemiluminiscence. In the latter determinations there was used as the chemiluminescent reagent a mixture of luminol, copper chloride and a carbonate buffer, having the following composition:

| | |
|---|---|
| 2 parts of luminol | $6.5 \times 10^{-3}$ molar |
| 1 part copper chloride $CuCl_2$ (catalyst) | $2 \times 10^{-2}$ molar |
| 1 part carbonate buffer (pH 10.3) | 8.3 g $Na_2CO_3$, 13.3 g $NaHCO_3$, 250 ml of distilled water. |
| 6 parts distilled water | |

The analyses were made in an apparatus such as that illustrated in FIG. 1.

The results obtained by the two methods agreed well with each other, as will be seen from the following Table:

| $H_2O_2$ (permanganate) | $H_2O_2$ (chemiluminescence) |
|---|---|
| 1.3 mg/l | 1.5 mg/l |
| 5.2 mg/l | 5.2 mg/l |
| 9.6 mg/l | 9.2 mg/l |

When the hydrogen peroxide content of the water from the mechanical pulp mill was to be determined by chemiluminescence, it was necessary to dilute the water 100 times in order to bring the hydrogen peroxide content to within a concentration suitable for measurement. The first analyses did not coincide with the permanganate titrations. It was found, however, that when the content of copper chloride was raised to 0.013 mole, agreement was reached between the permanganate titration and the chemiluminescence measurement, as will be seen from the following Table:

| $H_2O_2$ (permanganate) | $H_2O_2$ (chemiluminescence) |
|---|---|
| 5.2 g/l | 5.0 g/l |
| 3.2 g/l | 3.4 g/l |
| 4.5 g/l | 4.7 g/l |

The tests show that it is possible to measure continuously the content of hydrogen peroxide on a factory scale in a mechanical pulp mill, if the copper ion concentration is maintained at a sufficiently high level in the reagent solution.

By using a chemiluminescence measuring apparatus for determining the content of hydrogen peroxide in the waste water of the mechanical pulp factory, it was possible to follow continuously the variations in the peroxide content, thereby enabling the bleaching chemicals to be charged to the system in a manner such as to avoid overcharging and undercharging. When the system is manually superintended and charged, the content of hydrogen peroxide in the waste water normally varies between 0.2 and 0.8 g/1. By means of the method according to the invention, it was possible to maintain the content of hydrogen peroxide practically constant (0.4 – 0.5 g/1), which made possible considerable savings in peroxide (approximately 750 kg/day), and at the same time produced a more uniform pulp quality.

The aforementioned Examples are only a few of the possible applications of the invention. When bleaching sulphate pulp, the following bleaching sequences can be used for producing highly bleached pulp:

```
C E H D E D
C E C/D E D E D
O₂ C/D E D E D
``` where C is the chlorine stage, E the alkaline extraction stage, H the hypochlorite stage, D the chlorine dioxide stage, C/D the bleaching stage with a mixture of chlorine and chlorine dioxide, and $O_2$ the oxygen gas stage.

In all of these bleaching stages, the method according to the invention can be used to determine the content of bleaching agent, and therewith control of the amount of bleaching agent charged to the system. The invention can also be used to measure the chlorine dioxide content subsequent to charging sulphur dioxide to the system. The addition of sulphur dioxide is made to prevent corrosion, for example in the apparatus following the D-stage. The sulphur dioxide reacts instantaneously with the residues of chlorine dioxide. It is difficult to charge the exact amount of sulphur dioxide for this purpose. If, however, the chlorine dioxide content is first measured by the method according to the invention, the sulphur dioxide can then be charged in precise quantities, since it reacts stoichiometrically with chlorine dioxide.

In addition to its application to direct process control operations, the method according to the invention can also be used for measuring contents of liquids discharged to the environment. It is also possible to measure the content of gases, by washing the gas in a defined manner with a suitable liquid in which the gas can be dissolved (for example, sodium hydroxide solution can be used for chlorine in air), and the solution thereafter analysed.

The continuous method according to the invention affords a number of advantages over previously applied methods:

1. the process can be monitored more effectively than previously.
2. The measuring instrument (analytic apparatus) is of simple construction.
3. It is simple to measure extremely small quantities of light, thereby making it possible to detect and measure very low contents of chemicals.
4. A linear relationship exists between the signal and the concentration over a large concentration range.
5. The purity requirement on the chemiluminescent reagent is moderate, but it must be present during the analysis.
6. The method is inexpensive.
7. The analytic accuracy is very high.
8. Large amounts of substances can be determined by increasing the quantity of chemiluminescent reagent in relation to the quantity of bleaching agent in the liquid to be analysed.
9. The emission of light is practically independent of temperature.

Having regard to the foregoing disclosure, the following is claimed as the inventive and patentable embodiment thereof:

1. A process for controlling the quantity of oxidizing bleaching agent in a liquor for treating cellulosic material, which comprises continuously mixing such liquor containing such oxidizing bleaching agent with at least one chemiluminescent reagent selected from the group consisting of 1,3-aminophthalic acid hydrazide, N,N'-dimethylacridinium dinitrate, and 2,4,5-triphenyl imidazole, which reacts oxidatively therewith in a manner to emit light; continuously measuring the intensity of such light; determining the amount of such oxidizing bleaching agent in the liquor by comparison of the light intensity thus obtained with the light intensity for previously measured calibration values corresponding to known quantities of such oxidizing bleaching agent; and then from such determination controlling the addition of such oxidizing bleaching agent to the liquor, to maintain a desired quantity of such oxidizing bleaching agent in the liquor.

2. A process according to claim 1, in which a portion at least of the emitted light is impinged upon a photoelectric detector, to induce a signal whose response is related to the quantity of the oxidizing bleaching agent in the liquor.

3. A process according to claim 1, in which the liquor is a cellulose bleaching liquor, and the oxidizing bleaching agent is a cellulose bleaching agent.

4. A process according to claim 3, in which the bleaching agent is a chlorine compound.

5. A process according to claim 4, in which the chlorine compound is chlorine.

6. A process according to claim 4, in which the chlorine compound is a hypochlorite.

7. A process according to claim 4, in which the chlorine compound is chlorine dioxide.

8. A process according to claim 1, in which the liquor is a cellulose bleaching liquid and the oxidizing bleaching agent is a per compound selected from the group consisting of organic and inorganic peroxides, perborates and per acids.

9. A process according to claim 1, in which the liquor is a cellulose bleaching liquid and the oxidizing bleaching agent is oxygen or ozone.

10. A process according to claim 1, in which the chemiluminescent reagent is caused to react with at least two oxidizing bleaching agents present in the liquor to emit light, the oxidizing bleaching agents being reactive therewith under different conditions and measuring the light intensity from the reactions of the respective oxidizing bleaching agents at different times after mixing the reagent with liquor separately to determine the amounts of such oxidizing bleaching agents.

11. A process according to claim 10 in which the oxidizing bleaching agents are chlorine and chlorine dioxide, and the chemiluminescent reagent is 1,3-aminophthalic acid hydrazide.

12. A process according to claim 10 in which several chemiluminescent reagents are caused to react with several oxidizing bleaching agents present in said liquor, each reagent being specific for a specific oxidizing bleaching agent, and reacting therewith under different conditions; and measuring the light intensity from the reaction of such oxidizing bleaching agents under different conditions after mixing the reagents with the liquor separately to determine the amounts of oxidizing bleaching agents.

13. A process according to claim 1, in which the chemiluminescent reagent is 1,3-aminophthalic acid hydrazide.

14. A process according to claim 1, in which the chemiluminescent reagent is N,N'-dimethylacridinium dinitrate.

15. A process according to claim 1, in which the chemiluminescent reagent is 2,4,5-triphenyl imidazole.

* * * * *